(12) United States Patent
Al Thalab

(10) Patent No.: US 8,663,126 B1
(45) Date of Patent: Mar. 4, 2014

(54) WEARABLE ACOUSTIC DEVICE FOR MONITORING BREATHING SOUNDS

(71) Applicant: Fatemah S. Al Thalab, Alandalus (KW)

(72) Inventor: Fatemah S. Al Thalab, Alandalus (KW)

( * ) Notice: Subject to any disclaimer, the term of this patent is extended or adjusted under 35 U.S.C. 154(b) by 0 days.

(21) Appl. No.: 13/771,070

(22) Filed: Feb. 19, 2013

(51) Int. Cl.
*A61B 5/08* (2006.01)

(52) U.S. Cl.
USPC .......................................................... 600/529

(58) Field of Classification Search
USPC .................. 600/372, 390, 529, 532, 538, 534
See application file for complete search history.

(56) References Cited

U.S. PATENT DOCUMENTS

| | | | |
|---|---|---|---|
| 3,990,435 A | 11/1976 | Murphy | |
| 4,140,907 A * | 2/1979 | Oba | 250/316.1 |
| 5,165,417 A | 11/1992 | Murphy, Jr. | |
| 5,928,156 A | 7/1999 | Krumbiegel et al. | |
| 5,964,720 A | 10/1999 | Pelz | |
| 6,699,204 B1 | 3/2004 | Kehyayan et al. | |
| 7,942,824 B1 * | 5/2011 | Kayyali et al. | 600/538 |
| 2002/0097155 A1 * | 7/2002 | Cassel et al. | 340/573.1 |
| 2004/0236241 A1 | 11/2004 | Murphy | |
| 2005/0192508 A1 * | 9/2005 | Lange et al. | 600/534 |
| 2006/0077063 A1 | 4/2006 | Cheng et al. | |
| 2008/0082010 A1 * | 4/2008 | Juan | 600/502 |
| 2008/0082017 A1 | 4/2008 | Savic | |
| 2008/0183095 A1 | 7/2008 | Austin | |
| 2008/0317673 A1 | 12/2008 | Al-Thallab | |
| 2009/0076405 A1 * | 3/2009 | Amurthur et al. | 600/529 |

* cited by examiner

*Primary Examiner* — Michael D'Angelo
(74) *Attorney, Agent, or Firm* — Richard C. Litman

(57) ABSTRACT

The wearable acoustic device for monitoring breathing sounds includes an acoustic sensor and audible/visual indicators triggered by device electronics indicating normal, abnormal, and severity of abnormal bronchial asthmatic breathing. An elastic belt holds the device. Fasteners disposed on the belt allow the belt to be secured around the baby's chest. An oximeter may be connected to the device to measure percentage oxygen intake of the baby. A processor disposed in the device processes the oximeter and acoustic signals via an algorithmic sequence that looks for oxygen intake and the presence of bronchial asthmatic breathing vs. a normal breathing/oxygen intake sample stored in memory on the device. A transmitter powered by rechargeable batteries wirelessly transmits the alarm condition to the baby's caretaker. Depending on the normality/severity of the infant's breathing, an audible alarm sounds. The visual indicator displays severity of the breathing condition.

5 Claims, 3 Drawing Sheets

WEARABLE ACOUSTIC DEVICE FOR MONITORING BREATHING SOUNDS

BACKGROUND OF THE INVENTION

1. Field of the Invention

The present invention relates to baby monitors, and particularly to a wearable acoustic device for monitoring breathing sounds for the purpose of detecting bronchial asthma in an infant.

2. Description of the Related Art

Bronchial asthma typically causes decreased lung function, bronchial inflammation, coughing, wheezing and tightness in the chest. These problems are often exacerbated by airborne irritants, such as smoke, by exercise, by viral infections etc. When a patient encounters such problems, it means that the individual's airway is obstructed and the lungs are not receiving sufficient air. Typically, the airways become obstructed due to the lining of the airways becoming irritated and swollen and because the airways tighten, causing them to narrow. For infants, it is critical that the parent or other caregiver be alerted immediately when a bronchial asthma attack is imminent.

Thus, a wearable acoustic device for monitoring breathing sounds solving the aforementioned problems is desired.

SUMMARY OF THE INVENTION

The wearable acoustic device for monitoring breathing sounds includes a breathing detector and an audible and/or visual indicator triggered by device electronics to indicate normal versus abnormal breathing and the severity of abnormal bronchial asthmatic breathing. An elastic belt that can be placed around an infant's chest holds the device. Fasteners disposed on the belt allow the belt to be secured around the baby's chest. The detector includes a sensor, similar to a microphone, capable of detecting the baby's breathing patterns. An oximeter on the device also measure the percentage oxygen intake of the baby. A signal processor disposed in the device processes the oximeter and acoustic signals via an algorithmic sequence that looks for oxygen intake and the presence of bronchial asthmatic breathing vs. a normal breathing/oxygen intake sample stored in memory on the device. A transmitter powered by rechargeable batteries wirelessly transmits the alarm condition to the baby's caretaker. Depending on the normality/severity of the infant's breathing, an audible alarm sounds. The visual indicator displays the severity of the breathing condition.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
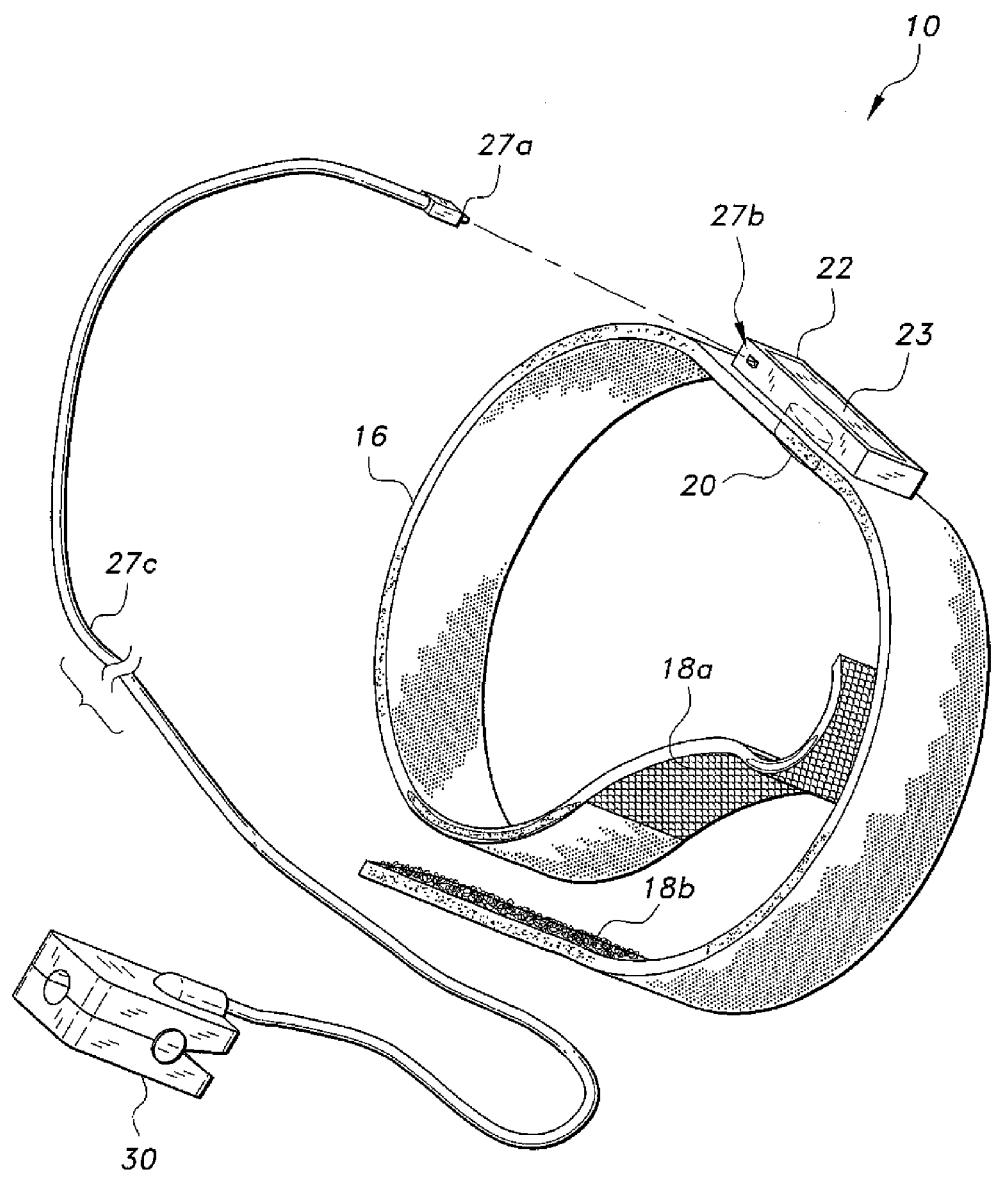
FIG. 1 is a perspective view of a wearable acoustic device for monitoring breathing sounds according to the present invention.
Figure 2:
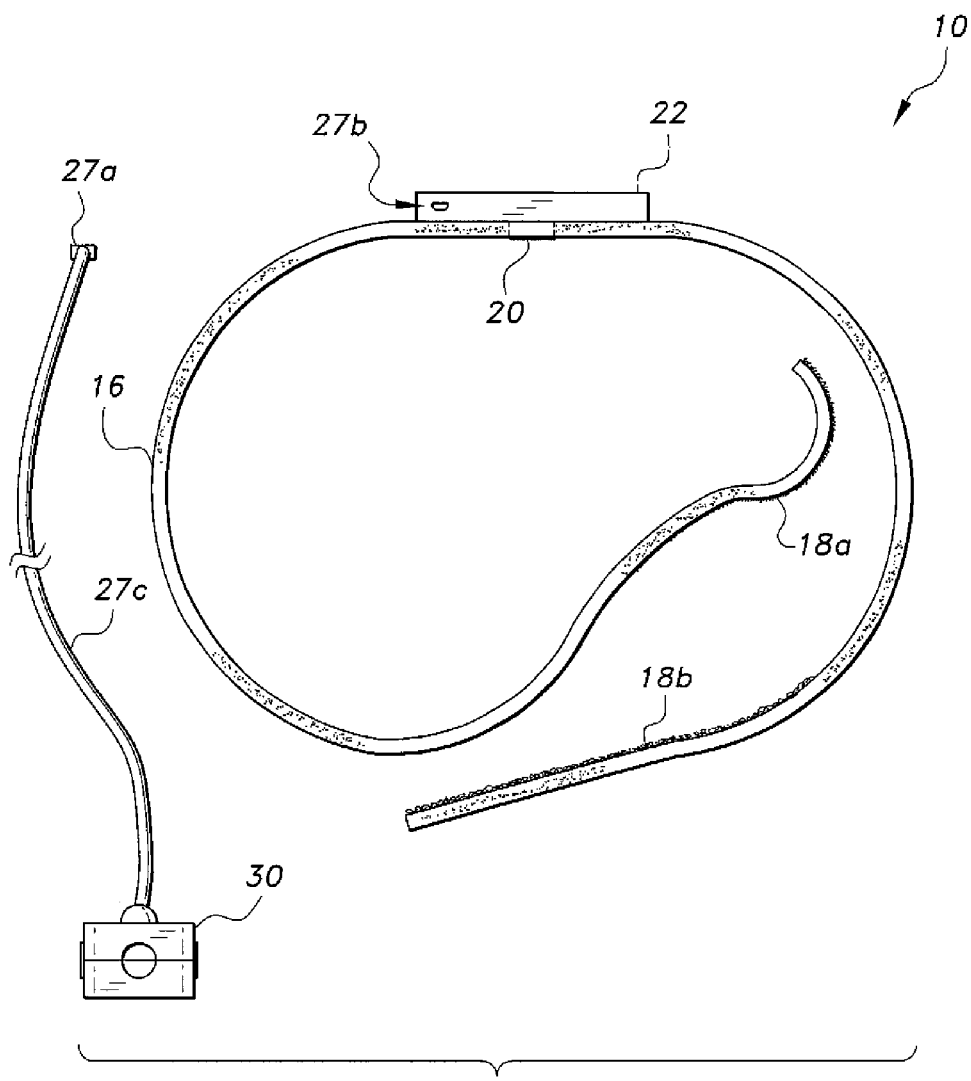
FIG. 2 is a top view of the wearable acoustic device of FIG. 1.
Figure 3:
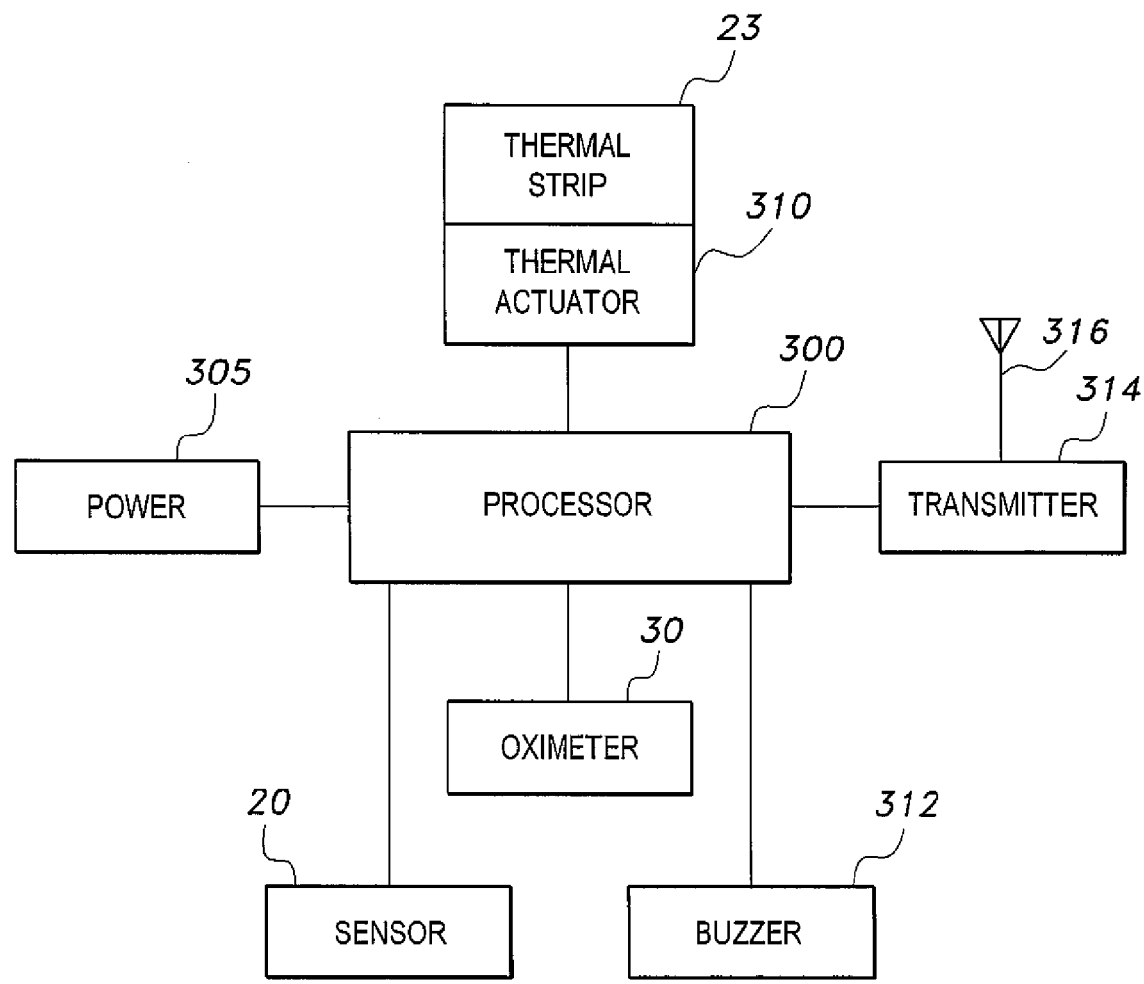
FIG. 3 is a block diagram of an electronic circuit for the wearable acoustic device of FIG. 1.

The wearable, acoustic device for monitoring breathing sounds, designated generally as 10 in FIGS. 1 and 2, comprises a sensor 20 removably attached to the chest of an infant by a resilient strap 16 having mating hook and loop fasteners 18a, 18b, thereby allowing the sensor 20 to continuously monitor the breathing sounds of the infant. As shown in FIG. 3, a processor (a microprocessor or a digital signal processor) or microcontroller 300 inside of a housing 22 receives a digital signal corresponding to the sounds picked up by the acoustic sensor 20 (piezoelectric or other type, as known in the art). The housing 22 is attached to the chest strap 16 and hermetically seals the electronic and other components disposed inside the housing 22. The hermetic seal provided by the housing 22 protects the electronics and other components from spills, moisture, and the like. The acoustic sensor 20 is disposed on the inside surface of the strap 16, opposite the housing 22, which is disposed on the outer surface of the strap 16. A profile of breathing sounds is stored in a memory circuit of the processor 300 (or a memory chip accessible by the processor 300), and the processor 300 performs signal processing to compare the profile sounds to the sounds of the child's breathing. The processor 300 may have programmed in it feature detectors operable on the real-time breathing sounds of an infant and the baseline normal breathing sounds stored in the processor's non-volatile memory to effect profile comparison of breathing sounds in order to determine whether or not and to what extent bronchial asthma is currently being presented in the infant. Representative abnormal breathing sounds may also be stored in non-volatile memory for comparison purposes. The wearable device 10 includes a visual indicator strip, such as a thermal strip 23, that shows a predetermined color to indicate whether the child is experiencing a particular stage of asthma and requires medical attention, as determined by the acoustic signal comparison performed by the processor 300.

A thermal actuator 310 connected to the processor 300 generates heat according to instructions from the processor 300, the heat being transmitted to the thermal strip 23 to change the strip's color accordingly. The thermal actuator 310 could be, for example, a configuration of high resistance wire designed to heat-up proportional to a current loop under control of processor 300. An oximeter 30 can be connected to the processor 300 via the port connector plug 27a connecting the oximeter cable 27c to the port receptacle 27b. The oximeter 30 may be attachable to the infant's finger. Real-time oxygen per-cent (SpO2) data from the oximeter is routed to the processor 300 so that the processor may compare the real-time data to data stored in the memory of the processor 300.

The oxygen percentage data from the oximeter 30, in relation to breathing sounds sensed by the sensor 20, is analyzed by the processor 300. The processor 300 triggers the various states of the indicator 23 based on its analysis of the SpO2 data from the oximeter 30 and the acoustic breathing data from the sensor 20. If the oximeter 30 is not connected, then the processor 300 triggers the various states of the indicator 23 based solely on analysis of the acoustic breathing data from the acoustic sensor 20.

The device 10 includes previously recorded normal/baseline breathing sounds, which are installed in the processor 300. The device 10 is placed on and secured to the infant's chest via strap 16. The chest wall of an infant is thin, with no big mass of muscles and fat, so the transmission of the chest sound is optimized by placement of the acoustic sensor 20 of the device 10 on the chest.

The alarm will be transmitted as a light or color indicator into three color categories (red, yellow and green), which indicate danger (in progress bronchial asthma attack), early stage bronchial asthma, and normal chest sound, respectively.

The alarm can be wirelessly transmitted via a transmitter 314 and antenna 316 to a mobile or portable device, e.g., a cellphone, in the possession of or proximate to the parent/caregiver. An audible alarm, such as a buzzer 312, may also be disposed in the housing 22 and may be triggered by the processor 300 during at least the danger-phase alarm condition.

The thermal actuator 310 and thermal strip 23 convert the vital signs into colors to estimate the severity of the breathing condition to the mother or caregiver. The device 10 is a way of detecting the severity of the bronchial asthma at home by a parent or caregiver. A power source 305 is disposed in the housing 22, and may be a rechargeable battery or other suitable portable source of power.

It will be understood that the diagrams in the Figures depicting the wearable acoustic device for monitoring breathing sounds 10 are exemplary only, and may be embodied in a dedicated electronic device having a microprocessor, microcontroller, digital signal processor, application specific integrated circuit, field programmable gate array, any combination of the aforementioned devices, or other device that combines the functionality of the wearable acoustic device for monitoring breathing sounds onto a single chip or multiple chips programmed to carry out the functions described herein, or may be embodied in a general purpose computer having the appropriate peripherals attached thereto and software stored on a computer readable media that can be loaded into main memory, volatile or non-volatile memory and executed by a processing unit to carry out the functionality of the apparatus described herein.

It is to be understood that the present invention is not limited to the embodiments described above, but encompasses any and all embodiments within the scope of the following claims.

I claim:

1. A wearable, acoustic device for monitoring breathing sounds, comprising:
    an elongate resilient strap having mating fasteners disposed on opposite ends thereof, the strap being adapted for removable attachment around a portion of a chest of an infant;
    a thin, flexible housing having a hermetic seal attached to an outer surface of the strap;
    an acoustic sensor disposed on an inner surface of the strap, the acoustic sensor contacting the portion of the chest of the infant when the strap is wrapped around the infant, the acoustic sensor generating a signal corresponding to the breathing sounds of an infant;
    a portable power source disposed in the housing for supplying electrical power to the wearable acoustic device;
    a processor disposed inside the housing, the acoustic sensor being operably connected to the processor, the processor having memory for storing the signal generated by the acoustic sensor and having a signal corresponding to baseline normal breathing sounds stored in memory, the processor having means for comparing the signal generated by the acoustic sensor to the stored signal corresponding to the baseline normal breathing sounds and generating a normal breathing output signal when the comparison of the signals indicates the infant is breathing normally, generating a warning output signal when the comparison of the signals indicates the infant is developing breathing problems, and generating a danger output signal when the comparison of the signals indicates the infant's breathing indicates an attack of bronchial asthma;
    a thermal actuator disposed in the housing and operably connected to the processor, the thermal actuator generating heat for changing the temperature of the thermal actuator in response to the output signal of the processor;
    a thermal activated color strip disposed on the housing and visible to a user when the strap is secured to the infant's chest, the thermal activated color strip being adjacent to the thermal actuator and changing color in response to the temperature of the thermal actuator, the thermal activated color strip being green in response to the temperature of the heat actuator due to a normal breathing output signal of the processor, yellow in response the temperature of the heat actuator due to a warning output signal of the processor, and red in response to the temperature of the heat actuator due to a danger output signal of the processor;
    an oximeter attachable to a finger of the infant; and
    a coupling between the oximeter and the processor.

2. The wearable, acoustic device according to claim 1, wherein the coupling further comprising:
    a cable extending from the oximeter, the oximeter transmitting percent oxygen (SpO2) data via the cable, the cable having an end connector; and
    a port disposed on said housing and accepting the end connector, the port being connected to said processor, thereby allowing said processor to receive the SpO2 data from the oximeter, said processor having means for analyzing the SpO2 data in conjunction with the comparison of the acoustic signal with the stored signal.

3. The wearable, acoustic device for monitoring breathing sounds according to claim 1, further comprising a wireless transmitter disposed in said housing, said wireless transmitter wirelessly sending an alarm to a user device when the processor generates a danger output signal.

4. The wearable, acoustic device for monitoring breathing sounds according to claim 1, wherein said hermetic seal for sealing components is disposed inside said housing from outside moisture and fluids.

5. A device for acoustic monitoring breathing sounds, wearable by a baby consisting of:
    an elongate resilient strap;
    mating fasteners disposed on opposite ends of the elongate resilient strap;
    wherein the mating fasteners and the strap being designed and configured for removable attachment around a chest portion of the baby;
    a hermetically sealed housing attached to an outer surface of the strap;
    wherein the hermetically sealed housing preventing outside moisture and fluids entering the housing;
    an acoustic sensor disposed on an inner surface of the strap;
    wherein when the strap is wrapped around the baby, the acoustic sensor is adapted for contacting the chest portion of the baby,
    whereby the acoustic sensor generates a signal corresponding to the breathing sounds of the baby;
    a power source disposed in the housing;
    the power source providing electrical power to the device;
    a processor disposed inside the housing, the acoustic sensor being operably connected to the processor, the processor having memory for storing the signal generated by the acoustic sensor and having a signal corresponding to baseline normal breathing sounds stored in memory, the processor also comparing the signal generated by the acoustic sensor to the stored signal corresponding to the baseline normal breathing sounds and generating a normal breathing output signal when the comparison of the signals indicates the baby is breathing normally, the processor generating a warning output signal when the comparison of the signals indicates the baby is developing breathing problems, and generating a danger output signal when the comparison of the signals indicates that the breathing of the baby indicating a bronchial asthma attack;

a thermal actuator disposed in the housing and operably connected to the processor, the thermal actuator generating heat for changing the temperature of the thermal actuator in response to the output signal of the processor;

a thermal activated color strip disposed on the housing and visible to a user when the strap is secured to the chest of the baby;

wherein the thermal activated color strip is in proximity to the thermal actuator and changes color in response to the temperature of the thermal actuator, the thermal activated color strip being green in response to a normal breathing output signal, yellow in response to a warning output signal, and red in response to a danger output signal;

an oximeter attachable to a finger of the baby, the oximeter providing percent oxygen (SpO2) data to the processor;

a cable extending from the oximeter;

an end connector on the cable, at an end opposite the oximeter;

a port disposed on the housing and accepting the end connector;

wherein the port is connected to the processor, thereby allowing the processor to receive the SpO2 data from the oximeter;

the processor further analyzing the SpO2 data in conjunction with the comparison of the acoustic signal with the stored signal; and a wireless transmitter disposed in the housing, the wireless transmitter wirelessly sending an alarm to a user device when the processor generates a danger output signal.

* * * * *